United States Patent
Whayne et al.

(10) Patent No.: US 7,780,661 B2
(45) Date of Patent: *Aug. 24, 2010

(54) VACUUM COAGULATION PROBES

(75) Inventors: James G. Whayne, Chapel Hill, NC (US); Sidney D. Fleischman, Durham, NC (US)

(73) Assignee: nContact Surgical, Inc, Morrisville, NC (US)

( * ) Notice: Subject to any disclaimer, the term of this patent is extended or adjusted under 35 U.S.C. 154(b) by 801 days.

This patent is subject to a terminal disclaimer.

(21) Appl. No.: 11/432,962

(22) Filed: May 12, 2006

(65) Prior Publication Data
US 2006/0235381 A1    Oct. 19, 2006

Related U.S. Application Data

(63) Continuation of application No. 10/425,251, filed on Apr. 29, 2003, now Pat. No. 7,063,698, which is a continuation-in-part of application No. 10/172,296, filed on Jun. 14, 2002, now Pat. No. 6,893,442.

(51) Int. Cl.
*A61B 18/18*  (2006.01)
(52) U.S. Cl. .......................... 606/49; 606/41
(58) Field of Classification Search ................. 606/33, 606/39, 41, 49
See application file for complete search history.

(56) References Cited

U.S. PATENT DOCUMENTS

| | | | |
|---|---|---|---|
| 5,125,928 A | 6/1992 | Parins et al. |
| 5,277,696 A | 1/1994 | Hagen |
| 5,322,064 A | 6/1994 | Lundquist |
| 5,366,490 A | 11/1994 | Edwards et al. |
| 5,562,722 A | 10/1996 | Racz et al. |
| 5,571,088 A | 11/1996 | Lennox et al. |
| 5,725,523 A | 3/1998 | Mueller |
| 5,733,280 A | 3/1998 | Avitall |

(Continued)

OTHER PUBLICATIONS

Cragg et al. "Endovascular Diathermic Vessel Occlusion", Radiology 1982, vol. 144, pp. 303-308.

(Continued)

*Primary Examiner*—Michael Peffley
*Assistant Examiner*—Samantha Good
(74) *Attorney, Agent, or Firm*—Levine Bagade Han LLP

(57) ABSTRACT

An embodiment of the invention includes a surgical device for coagulating soft tissue such as atrial tissue in the treatment of atrial fibrillation, atrial flutter, and atrial tachycardia; tendon or ligament shrinkage; or articular cartilage removal. The surgical device integrates a suction mechanism with the coagulation mechanism improving the lesion creation capabilities of the device. The surgical device comprises an elongate member having an insulative covering attached about conductive elements capable of coagulating soft tissue when radiofrequency or direct current energy is transmitted to the conductive elements. Openings through the insulative covering expose regions of the conductive elements and are coupled to lumens in the elongate member which are routed to a vacuum source. Suction causes the soft tissue to actively engage the opening thus the integrated, exposed conductive elements to facilitate the coagulation process and ensure the lesions created are consistent, continuous, and transmural. The embodiments of the invention can also incorporate cooling mechanisms associated with the conductive elements and coupled to a fluid source to passively transport fluid along the contacted soft tissue surface to cool thus pushing the maximum temperature deeper into tissue.

17 Claims, 12 Drawing Sheets

U.S. PATENT DOCUMENTS

| | | | |
|---|---|---|---|
| 5,769,847 | A | 6/1998 | Panescu et al. |
| 5,782,828 | A | 7/1998 | Chen et al. |
| 5,785,706 | A | 7/1998 | Bednarek |
| 5,788,681 | A | 8/1998 | Weaver et al. |
| 5,836,311 | A | 11/1998 | Borst et al. |
| 5,851,206 | A | 12/1998 | Guglielmi et al. |
| 5,919,188 | A | 7/1999 | Shearon et al. |
| 5,957,882 | A | 9/1999 | Nita et al. |
| 5,971,983 | A | 10/1999 | Lesh |
| 6,063,081 | A | 5/2000 | Mulier et al. |
| 6,071,279 | A | 6/2000 | Whayne et al. |
| 6,071,281 | A | 6/2000 | Burnside et al. |
| 6,080,151 | A | 6/2000 | Swartz et al. |
| 6,161,543 | A | 12/2000 | Cox et al. |
| 6,190,382 | B1 | 2/2001 | Ormsby et al. |
| 6,210,408 | B1 | 4/2001 | Chandrasekaran et al. |
| 6,237,555 | B1 | 5/2001 | Dykstra et al. |
| 6,237,605 | B1 | 5/2001 | Vaska et al. |
| 6,237,606 | B1 | 5/2001 | Zikorus et al. |
| 6,264,650 | B1 | 7/2001 | Hovda et al. |
| 6,264,654 | B1 | 7/2001 | Swartz et al. |
| 6,296,638 | B1 | 10/2001 | Davison et al. |
| 6,305,378 | B1 | 10/2001 | Lesh |
| 6,311,692 | B1 | 11/2001 | Vaska et al. |
| 6,314,916 | B1 | 11/2001 | Watson, Sr. |
| 6,314,962 | B1 | 11/2001 | Vaska et al. |
| 6,314,963 | B1 | 11/2001 | Vaska et al. |
| 6,364,876 | B1 | 4/2002 | Erb et al. |
| 6,425,895 | B1 | 7/2002 | Swanson et al. |
| 6,463,223 | B1 | 10/2002 | Karakama et al. |
| 6,463,332 | B1 | 10/2002 | Aldrich |
| 6,464,699 | B1 | 10/2002 | Swanson |
| 6,474,340 | B1 | 11/2002 | Vaska et al. |
| 6,482,202 | B1 | 11/2002 | Goble et al. |
| 6,484,727 | B1 | 11/2002 | Vaska et al. |
| 6,506,180 | B1 | 1/2003 | Lary |
| 6,514,250 | B1 | 2/2003 | Jahns et al. |
| 6,558,382 | B2 | 5/2003 | Jahns et al. |
| 6,579,288 | B1 | 6/2003 | Swanson et al. |
| 6,605,087 | B2 | 8/2003 | Swartz et al. |
| 6,645,200 | B1 | 11/2003 | Koblish et al. |
| 6,645,202 | B1 | 11/2003 | Pless et al. |
| 6,652,518 | B2 | 11/2003 | Wellman et al. |
| 6,663,622 | B1 | 12/2003 | Foley et al. |
| 6,689,128 | B2 | 2/2004 | Sliwa, Jr. et al. |
| 6,701,931 | B2 | 3/2004 | Sliwa, Jr. et al. |
| 6,719,755 | B2 | 4/2004 | Sliwa, Jr. et al. |
| 6,726,684 | B1 | 4/2004 | Woloszko et al. |
| 6,764,487 | B2 | 7/2004 | Mulier et al. |
| 6,849,075 | B2 | 2/2005 | Bertolero et al. |
| 6,887,238 | B2 | 5/2005 | Jahns et al. |
| 6,887,249 | B1 | 5/2005 | Houser et al. |
| 6,893,442 | B2 * | 5/2005 | Whayne .............. 606/49 |
| 6,917,834 | B2 | 7/2005 | Koblish et al. |
| 6,949,095 | B2 | 9/2005 | Vaska et al. |
| 7,033,352 | B1 * | 4/2006 | Gauthier et al. ............... 606/33 |
| 7,052,491 | B2 | 5/2006 | Erb et al. |
| 7,063,698 | B2 * | 6/2006 | Whayne et al. .............. 606/49 |
| 7,115,126 | B2 | 10/2006 | Berube et al. |
| 7,144,363 | B2 | 12/2006 | Pai et al. |
| 7,207,988 | B2 | 4/2007 | Leckrone et al. |
| 7,226,448 | B2 | 6/2007 | Bertolero et al. |
| 7,371,233 | B2 | 5/2008 | Swanson et al. |
| 7,387,627 | B2 | 6/2008 | Erb et al. |
| 7,399,300 | B2 | 7/2008 | Bertolero et al. |
| 7,410,487 | B2 * | 8/2008 | Whayne ............... 606/49 |
| 7,572,257 | B2 * | 8/2009 | Whayne et al. .............. 606/49 |
| 2002/0072739 | A1 | 6/2002 | Lee et al. |
| 2002/0091299 | A1 | 7/2002 | Silverman et al. |
| 2002/0111608 | A1 | 8/2002 | Baerveldt et al. |
| 2003/0233091 | A1 | 12/2003 | Whayne et al. |
| 2004/0153057 | A1 | 8/2004 | Davison |
| 2005/0149152 | A1 | 7/2005 | Bertolero et al. |
| 2005/0240175 | A1 | 10/2005 | Bertolero et al. |
| 2005/0288666 | A1 | 12/2005 | Bertolero et al. |
| 2006/0004388 | A1 | 1/2006 | Whayne et al. |
| 2006/0009762 | A1 | 1/2006 | Whayne |
| 2006/0015165 | A1 | 1/2006 | Bertolero et al. |
| 2006/0184167 | A1 | 8/2006 | Vaska et al. |
| 2006/0200124 | A1 | 9/2006 | Whayne et al. |
| 2006/0206113 | A1 * | 9/2006 | Whayne et al. ............... 606/49 |
| 2006/0235381 | A1 | 10/2006 | Whayne et al. |
| 2006/0293646 | A1 | 12/2006 | Whayne et al. |
| 2007/0043351 | A1 * | 2/2007 | Fleischman et al. ........... 606/49 |
| 2007/0083082 | A1 | 4/2007 | Kiser et al. |
| 2007/0083225 | A1 | 4/2007 | Kiser et al. |
| 2007/0156185 | A1 | 7/2007 | Swanson et al. |
| 2007/0239155 | A1 | 10/2007 | Ibrahim et al. |
| 2007/0249991 | A1 | 10/2007 | Whayne et al. |
| 2007/0250058 | A1 | 10/2007 | Whayne et al. |
| 2008/0114342 | A1 | 5/2008 | Whayne et al. |
| 2008/0114354 | A1 * | 5/2008 | Whayne et al. ............... 606/49 |
| 2008/0114355 | A1 | 5/2008 | Whayne et al. |
| 2008/0243119 | A1 * | 10/2008 | Whayne ...................... 606/49 |

OTHER PUBLICATIONS

Gorisch et al. "Heat-Induced Contraction of Blood Vessels", Lasers in Surgery and Medicine 1982, vol. 2, pp. 1-13.

Nath et al. "Cellular Electrophysiologic Effects of Hyperthermia On Isolated Guinea Pig Papillary Muscle: Implications for Catheter Ablation", Circulation 1993, vol. 88, pp. 1826-1831.

International Patent Application No. PCT/US2006/015009 in the name of Fleischman et al. filed Apr. 21, 2006, International Search Report and Written Opinion mailed Sep. 27, 2006.

International Patent Application No. PCT/US20061060753 in the name of Whayne et al. filed Nov. 9, 2006, International Search Report and Written Opinion mailed Dec. 3, 2007.

U.S. Appl. No. 10/172,296, filed Jun. 14, 2002 in the name of Whayne, Non-Final Office Action mailed Oct. 17, 2003.

U.S. Appl. No. 10/172,296, filed Jun. 14, 2002 in the name of Whayne, Notice of Allowance mailed Jul. 23, 2004.

U.S. Appl. No. 10/425,251, filed Apr. 29, 2003 in the name of Whayne, Final Office Action mailed Nov. 14, 2005.

U.S. Appl. No. 10/425,251, filed Apr. 29, 2003 in the name of Whayne, Non-final Office Action mailed Jan. 20, 2006.

U.S. Appl. No. 10/425,251, filed Apr. 29, 2003, in the name of Whayne, Non-final Office Action mailed May 25, 2005.

U.S. Appl. No. 10/425,251, filed Apr. 29, 2003 in the name of Whayne, Notice of Allowance mailed Apr. 12, 2006.

U.S. Appl. No. 11/096,205, filed Mar. 30, 2005 in the name of Whayne, Non-final Office Action mailed Sep. 19, 2007.

U.S. Appl. No. 11/096,205, filed Mar. 30, 2005 in the name of Whayne, Notice of Allowance mailed May 1, 2008.

U.S. Appl. No. 11/208,465, filed Aug. 18, 2008 in the name of Whayne et al., Final Office Action mailed Jan. 7, 2009.

U.S. Appl. No. 11/208,465, filed Aug. 18, 2008 in the name of Whayne et al., Non-final Office Action mailed Jul. 29, 2008.

U.S. Appl. No. 11/208,465, filed Aug. 18, 2008 in the name of Whayne et al., Notice of Allowance mailed Jun. 11, 2009.

U.S. Appl. No. 11/419,840, filed May 23, 2006 the name of Whayne, Non-final Office Action mailed Aug. 31, 2009.

U.S. Appl. No. 11/433,248, filed May 12, 2006 in the name of Whayne, Non-final Office Action mailed Jan. 5, 2009.

U.S. Appl. No. 11/433,248, filed May 12, 2006 in the name of Whayne, Non-final Office Action mailed Sep. 3, 2009.

U.S. Appl. No. 11/558,423, filed Nov. 9, 2006 in the name of Whayne et al., Non-final Office Action mailed Aug. 19, 2009.

* cited by examiner

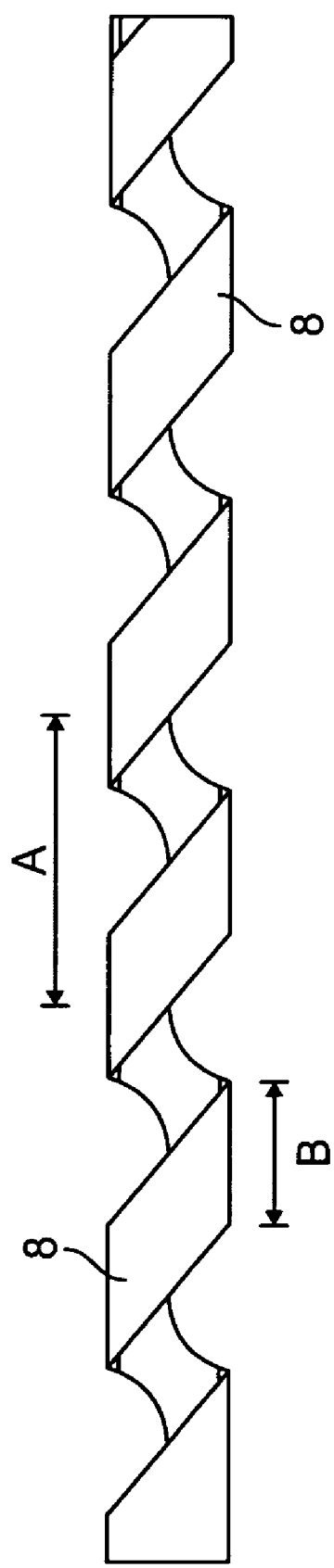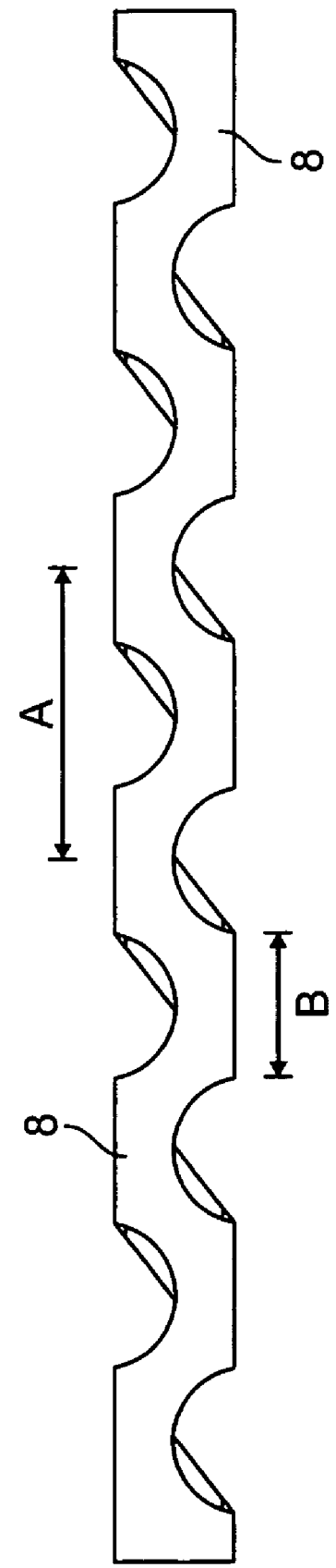
FIG. 3A
FIG. 3B

VACUUM COAGULATION PROBES

CROSS-REFERENCE TO RELATED APPLICATIONS

This application is a continuation of U.S. patent application Ser. No. 10/425,251 filed Apr. 29, 2003 now U.S. Pat. No. 7,063,698 which is a continuation-in-part of U.S. patent application Ser. No. 10/172,296 filed Jun. 14, 2002 now U.S. Pat. No. 6,893,442, the contents of which are incorporated herein by reference in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

REFERENCE TO AN APPENDIX SUBMITTED ON COMPACT DISC

Not Applicable

BACKGROUND OF THE INVENTION

Atrial fibrillation surgery involving radiofrequency, d.c., microwave, or other thermal ablation of atrial tissue has a limitation in that tissue contact throughout the length of the electrode(s) is/are not consistent causing variability in the transmission of energy throughout the target length of ablated/coagulated tissue. This produces gaps of viable tissue that promote propagation of wavelets that sustain atrial fibrillation, or produce atrial flutter, atrial tachycardia, or other arrhythmia substrate.

Another influence in the inability of existing thermal ablation probes to create complete curvilinear, transmural lesions is the presence of convective cooling on the opposite surface of the atrium producing a heat sink that decreases the maximum temperature at this surface thereby preventing the lesions from consistently extending transmural through the entire wall of the atrium. This is especially relevant during beating-heart therapies in which the coagulation/ablation probe is placed against the epicardial surface, and blood flowing along the endocardium removes heat thus producing a larger gradient between temperature immediately under the probe electrodes along the epicardium and that at the endocardium. Increased tissue contact is capable of reversing this effect by evoking a compression of the tissue that shortens the wall thickness of the atria, ensuring consistent contact throughout the length of the electrode(s), and increasing the efficiency of thermal conduction from the epicardium to the endocardium. As such a more consistent and reliable lesion is created.

Another deficiency of current approaches is the ability to direct the coagulation to precise regions of soft tissue while avoiding underlying or nearby tissue structures. For example, atrial fibrillation ablation may involve extending a lesion to the annulus near which the circumflex, right coronary artery, and coronary sinus reside. Conventional approaches are unable to selectively ablate desired soft tissue structures and isolate preserved tissue structures from targeted regions.

The embodiments of the invention address these deficiencies for atrial fibrillation ablation. In addition, the embodiments of the invention address similar deficiencies that are apparent during other applications involving coagulation of a selected-tissue region in a precise manner such as tendon shrinking and articular cartilage removal.

BRIEF SUMMARY OF THE INVENTION

Embodiments of the invention relate to devices and methods for less invasive treatment of atrial fibrillation, tendon or ligament shrinkage, and articular cartilage removal. More particularly, certain embodiments of the invention relate to ablation and/or coagulation probes that integrate suction to the coagulation electrodes so as to ensure consistent and intimate tissue contact directly between the electrodes and soft tissue. These integrated vacuum-assisted coagulation probes are capable of reliably creating transmural, curvilinear lesions capable of preventing the propagation of wavelets that initiate and sustain atrial fibrillation, atrial flutter, or other arrhythmia substrate. The vacuum-assisted coagulation probes also facilitate less invasive surgery involving endoscopic or laparoscopic access and visualization to the target coagulation sites. Additionally, the vacuum-assisted coagulation probes of the invention are suitable for coagulating soft tissues (e.g. atrial tissue to treat atrial fibrillation, atrial flutter, or other arrhythmia) through a median sternotomy, lateral thoracotomy, intercostals port-access, mini-sternotomies, other less invasive approaches involving subxiphoid access, inguinal approaches, or sub-thoracic approaches adjacent the diaphram. Alternatively, the vacuum-assisted coagulation probes can be modified for catheter-based applications by elongating the shaft, altering the dimensions of the device, and incorporating other feature tailored for intravascular access.

The vacuum-assisted coagulation probes can also be used to coagulate other soft tissues for a variety of applications including cancer therapy (e.g. liver, prostate, colon, esophageal, gastrointestinal, gynecological, etc.); GERD treatment; shrinking of collagen-based tissue structures such as skin, tendons, muscles, ligaments, vascular tissue during arthroscopic, laparoscopic, or other minimally invasive procedures; and/or coagulation of an upper layer of tissue without damaging underlying tissue structures, for example during articular cartilage removal.

BRIEF DESCRIPTION OF THE SEVERAL VIEWS OF THE DRAWINGS

Several exemplary embodiments of the present invention, and many features and advantages of those exemplary embodiments will be elaborated in the following detailed description and accompanying drawings, in which:

FIGS. 3A and 3B show a bottom view and a top view of another electrode embodiment for an integrated vacuum coagulation probe;

DETAILED DESCRIPTION OF THE INVENTION

Figure 1A:
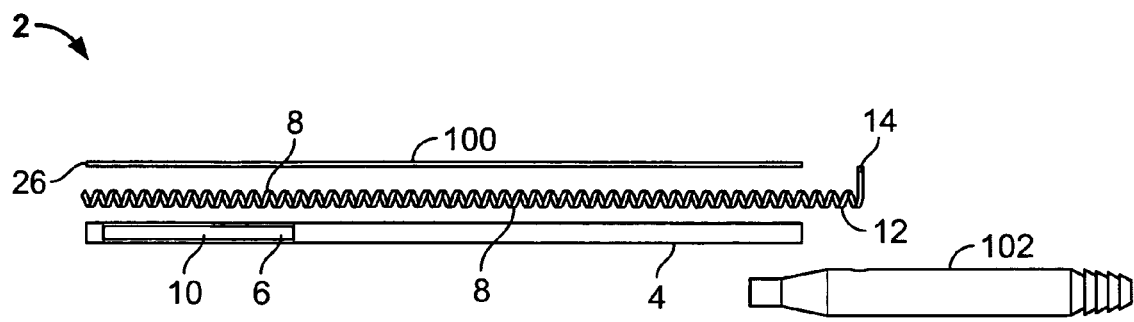
FIGS. 1A to 1C show an exploded view, a bottom view, a close-up view of an integrated vacuum coagulation probe embodiment of the invention.

A need exists for integrated vacuum coagulation probe devices and methods that create contiguous, curvilinear, transmural lesions in the atria to treat atrial fibrillation, atrial flutter, ventricular tachycardia, or other arrhythmia substrate. In addition, such devices and methods could simplify and improve other soft tissue coagulation procedures by ensuring intimate tissue contact while precisely and effectively heating a region of soft tissue. For example, tendon shrinking during arthroscopic procedures and articular cartilage fragment removal from bony tissue are facilitated and controlled with the embodiments of the invention. The embodiments of the invention also enable pharmacologically modifying tissue structures with localized administration of agents to cross-link or otherwise adapt tissue to specific needs.

The needed technology also could enable certain procedures to be performed less invasively through limited incisions that previously required large, open incisions with inherent morbidity and risks to other anatomic structures. Such inventive devices and methods thus could enable patients to undergo such reparative or therapeutic surgical procedures while enduring less pain, expedited hospital stays, and shorter rehabilitative and recovery times.

The present invention relates to methods and devices that enable reliable and controlled coagulation of soft tissue during less invasive procedures. To accomplish this, the coagulation probe incorporates vacuum conduits integrated with the electrode(s) to urge the soft tissue into intimate contact with the strategically-located edges of the electrode(s) and ensure efficient transmission of energy capable of consistently and completely heating a desired region of soft tissue. The integrated vacuum coagulation probe embodiments of the invention also enable passive convective cooling of the tissue surface by using the vacuum source to transport fluid along the tissue surface from a fluid source without the need for a separate injector or pump. Convective cooling directs the maximum temperature deeper into tissue thereby enabling the delivery of increased energy into the tissue and creating larger and deeper lesions.

The following is a detailed description of certain exemplary embodiments of the inventions. This detailed description is not to be taken in a limiting sense, but is made merely for the purpose of illustrating certain general principles of the inventions.

This patent application discloses a number of exemplary embodiments, mainly in the context of soft tissue coagulation accomplished through less invasive approaches (e.g. thoracoscopic, arthroscopic, laparoscopic, percutaneous, or other minimally invasive procedures). The integrated vacuum coagulation probe embodiments disclosed herein produce intimate contact between a soft tissue surface and electrode(s) used to transmit energy capable of heating the soft tissue until irreversible injury is achieved making the soft tissue non-viable and unable to propagate electrical impulses, mutate, or reproduce. The integrated vacuum coagulation probe embodiments also enable supporting and/or repositioning the soft tissue during coagulation to prevent or minimize shrinking or other change in the shape of the soft tissue associated with heat causing the collagen in the soft tissue to denature.

Nevertheless, it should be appreciated that the integrated vacuum coagulation probe devices can be applicable for use in other indications involving devices that are used to coagulate soft tissue where access to the tissue is limited by a small opening into the cavity, confined space at the soft tissue interface, difficult to reach locations, or other anatomic limitation. The embodiments of the invention can be configured for the human anatomy; however, it should be noted that the embodiments of the invention can, in some cases, be tailored to other species, such as canine, ovine, porcine, bovine, or horses, by changing the geometry and sizes of the structures.

An additional benefit of integrated vacuum coagulation probe devices can involve the ease of deployment and the rapid healing post-procedure. The small incision used to access the soft tissue during such procedures accelerates the healing process and reduces the visible scar. The integrated vacuum coagulation probe devices can be capable of being deployed through a thoracostomy, thoracotomy, median sternotomy, mini-sternotomy, mini-thoracotomy, xiphoid access, subthoracic access, arthroscopic, or laparoscopic approach, thereby potentially eliminating the need for long incisions to access the soft tissue and corresponding anatomic structures.

The integrated vacuum coagulation probe, and corresponding components, can be fabricated from at least one rod, wire, band, bar, tube, sheet, ribbon, other raw material having the desired pattern, cross-sectional profile, and dimensions, or a combination of cross-sections. The rod, wire, band, bar, sheet, tube, ribbon, or other raw material can be fabricated by extruding, injection molding, press-forging, rotary forging, bar rolling, sheet rolling, cold drawing, cold rolling, using multiple cold-working and annealing steps, casting, or otherwise forming into the desired shape. The components of the integrated vacuum coagulation probe may be cut from raw material by conventional abrasive sawing, water jet cutting, laser cutting, ultrasonic cutting, EDM machining, photochemical etching, or other techniques to cut the lumens, pores, ports and/or other features of the vacuum coagulation probe from the raw material. Components of the integrated vacuum coagulation probe can be bonded by laser welding, adhesives, ultrasonic welding, radiofrequency welding, soldering, spot welding, or other attachment means.

For several of the integrated vacuum coagulation probe embodiments below, various components can be fabricated from at least one wire, tube, ribbon, sheet, rod, band or bar of raw material cut to the desired configuration and thermally formed into the desired 3-dimensional configuration. When thermally forming (e.g. annealing) components, they can be stressed into the desired resting configuration using mandrels and/or forming fixtures having the desired resting shape of the puncturing component, and heated to between 300 and 600 degrees Celsius for a period of time, typically between 15 seconds and 10 minutes. Alternatively, the components may be heating immediately prior to stressing. Once the volume of material reaches the desired temperature, the component is quenched by inserting into chilled or room temperature water or other fluid, or allowed to return to ambient temperature. As such the components can be fabricated into their resting configuration. When extremely small radii of curvature are desired, multiple thermal forming steps can be utilized to sequentially bend the component into smaller radii of curvature.

When fabricating the integrated vacuum coagulation probe components from tubing, the raw material can have an oval, circular, rectangular, square, trapezoidal, or other cross-sectional geometry capable of being cut into the desired pattern. After cutting the desired pattern of lumens, ports, and pores, the components can be formed into the desired shape, stressed, heated, for example, between 300° C. and 600° C., and allowed to cool in the preformed geometry to set the shape of the components, as discussed above.

Once the components are fabricated and formed into the desired 3-dimensional geometry, they can be tumbled, sand blasted, bead blasted, chemically etched, ground, mechanically polished, electropolished, or otherwise treated to remove any edges and/or produce a smooth surface.

Holes, slots, notches, other cut-away areas, or regions of ground material can be incorporated in the components to tailor the stiffness profile. Cutting and treating processes described above can be used to fabricate the slots, holes, notches, cut-away regions, and/or ground regions in the desired pattern to taper the stiffness along, focus the stiffness along the length of, reinforce specific regions of, or otherwise customize the stiffness profile of the vacuum probe components.

Figure 1B:
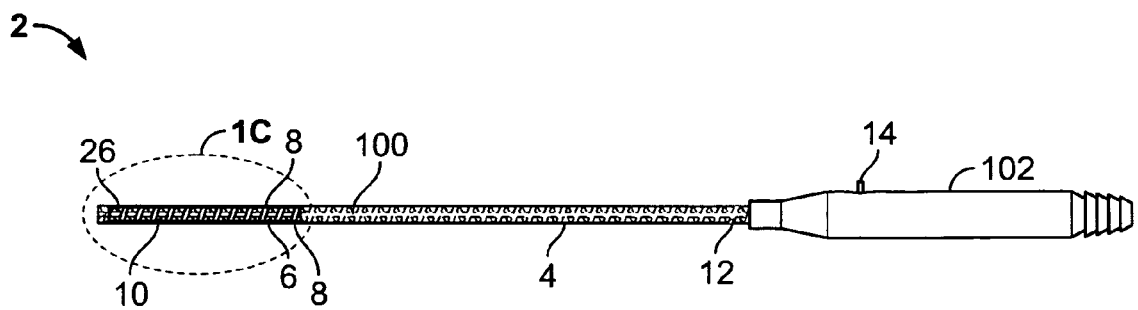
Figure 1C:
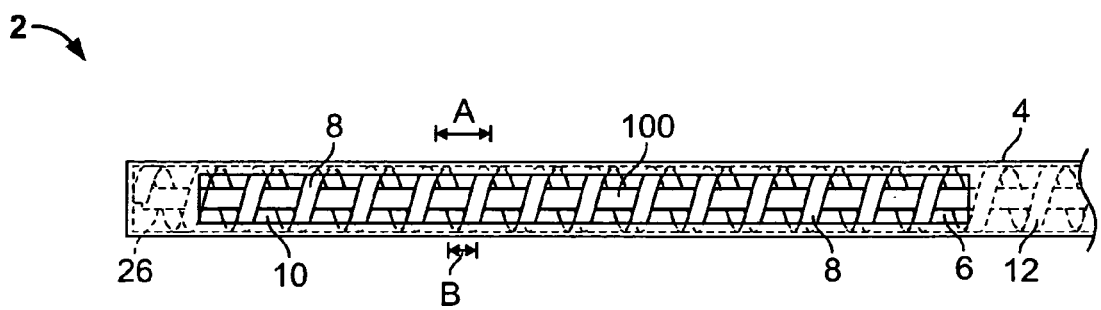

FIGS. 1A to 1C show an exploded view, a side view, and a close-up view of an integrated vacuum coagulation probe 2 embodiment of the invention. The integrated vacuum coagulation probe 2 incorporates a shaft 4 that defines a lumen 6, as shown in FIG. 1A.

The shaft 4 in the illustrated embodiment is fabricated from a polymer such as PEBAX®, polyester, polyurethane, urethane, silicone, polyimide, other thermoplastic, thermoset plastic, or elastomer. Alternatively, the shaft may be a metal (e.g. titanium, etc.), or metal alloy (e.g. stainless steel, spring steel, nickel titanium, etc.) fabricated as a cut tube, braided wires, a mesh, one or more helically wound wires, or other configuration encapsulated in or covered by a polymer. When using polymer coverings/insulation over the electrode(s) 8 and/or the shaft 4, the covering/insulation may be extruded, injection molded (especially when incorporating discrete features such as the opening without requiring another step of cutting the covering/insulation around the defined electrode), dipped, or applied using another manufacturing process involving, embedding or covering the electrode and/or shaft support structures with the polymer covering The shaft shown in FIGS. 1A to 1C consists of a polymer, as listed above, covering or encapsulating a rectangular (or elliptical or circular) wire wound into a helix (or mesh, or other geometry) throughout a majority of the probe length with a section of the polymer removed from the encapsulated or covered wire to create the suction pore(s) or opening(s) 10 that are coupled to lumen 6, and expose the conductive surface of the wire and define the electrode 8. As such, the embodiment in FIGS. 1A to 1C consists of a probe fabricated from four components: 1) a fluid injection/support tube 100 that incorporates at least one aperture 26 at its distal end; 2) an electrode/shaft support coil 8 connected to an electrical conduit 12 that is coupled to a connector 14 at the handle 102; 3) a shaft 4 defining at least one pore/opening 10; and 4) a handle 102 that houses at least one electrical connector 14 and ports that attach to the lumen 6 of the shaft 4 and the lumen of the fluid injection/support tube 100. Alternatively, the section of the probe containing the exposed conductive element of the electrode 8 and the cut-out region(s) of the covering that defines the suction pore(s)/opening(s) may be fabricated from separate component(s) than the shaft 4.

The shaft and/or distal section of the probe housing the electrode 8 and suction pore(s)/opening(s) 10 may have a circular cross-section, elliptical cross-section, rectangular cross-section, or other geometry depending on the stiffness requirements, access characteristics, and other considerations. The shaft 4 may be fabricated as a multi-lumen tubing having two or more separate lumens serving specific functions. At its proximal end, the shaft 4 is bonded to a handle 102 that incorporates at least one port that feeds the shaft lumen(s) 6 and the lumen of the injection/support tube 100. The port(s) may incorporate luer adaptor(s) or other tubing connector(s) to facilitate attaching IV tubing, surgical tubing, or other tube capable of connecting to a vacuum source.

The handle 102 also houses at least one electrical connector 14 to-which wire(s) 12 are attached at the proximal end. The wire(s) 12 are routed to the electrode(s) 8 to enable transmitting energy (radiofrequency, or direct current) to the electrode(s). In the embodiment in FIGS. 1A to 1C, the helical wire functions as the electrode 8 and the signal wire 12. When the electrode is not integral to the shaft, discrete signal wire(s) 12 are secured to the electrode 8 and are routed to the electrical connector 14 at the handle 102. When transmitting radiofrequency energy in unipolar fashion between at least one electrode 8 and a large surface area, reference electrode (not shown), a single wire 12 is routed to each electrode and connected to a radiofrequency generator. When transmitting d.c. or radiofrequency energy in bipolar fashion between pairs of electrodes 8, individual wires 12 are connected to each of two or more individual, closely-spaced electrodes 8 and RF or DC energy is applied between the electrodes. When utilizing resistive heating of the electrode 8 and relying on conduction to transfer heat to contacted tissue, two wires 12 are connected to each electrode 8 (e.g. resistive element in this case) separated by a length defining the region to be heated so the tissue contacting length of the electrode 8 heats to the desired temperature and the heat is conducted to contacted tissue.

Temperature sensors (not shown) may be associated with each electrode 8 with wires routed along the shaft to the handle where they are connected to an electrical connector (14) capable of transmitting the temperature signal to a radiofrequency generator with temperature monitoring or control capabilities or a separate temperature monitor. U.S. Pat. No. 5,769,847, entitled "Systems and methods for controlling tissue ablation using multiple temperature sensing elements" and incorporated herein by reference, describes tissue coagulation systems utilizing multiple electrodes and temperature sensors associated with each electrode to controllably transmit radiofrequency energy and maintain all electrode(s) essentially at the same temperature. The vacuum coagulation probe electrode(s) and associated temperature sensors (not shown) may be connected to such a mechanism to control transmission of radiofrequency energy to each electrode to control the heating of contacted soft tissue.

The integrated vacuum coagulation probe embodiment in FIGS. 1A to 1C exposes the electrode 8 only along one side of the integrated vacuum coagulation probe and insulates the opposite side against transmission of radiofrequency energy and/or heat. As shown in FIGS 1A to 1C, at least one pore or opening 10 is created along one side of the coagulation probe through the side wall of the covering/insulation to expose the conductive surface of the helical wire and coupling the lumen 6 of the shaft 4 to the exposed surface of the helical wire thereby defining the integrated electrode(s) 8. These openings 10 enable producing a vacuum against the soft tissue throughout the length of electrode(s) 8 thereby ensuring intimate tissue contact between the electrode(s) 8 and the soft tissue. The openings 10 also orient the edges of the electrode(s) 8, commonly associated with high current densities transmitted into the soft tissue, to create a continuous, consistent lesion throughout the length of the electrode(s) 8 without producing hot spots that interfere with creating lesions having consistent depth and width. The combination of creating intimate tissue contact and directing the current density profile creates controlled and efficient heating of the soft tissue required when coagulating tissue to produce defined lengths of transmural lesions in atrial tissue (or other soft tissue). The pore(s)/opening(s) may have a constant width or vary along the length of the electrode 8 to adjust contact forces and/or current density profiles throughout the length of the electrode(s) 8.

The electrode(s) 8 may be fabricated from metal (e.g. tungsten, titanium, tantalum, platinum, gold, silver), metal alloy (e.g. stainless steel, spring steel, nickel titanium, platinum iridium, silver chloride, etc.), metals deposited over a carrier (e.g. gold-plated stainless steel, gold deposited polyimide, platinum deposited polyester, etc.) or a combination of materials fabricated, with methods described previously, to define the shape, the coil/winding width B, the coil pitch A or separation (for non-helical configurations), shaft 4 attachment features (e.g. threads, slots, etc.) or other features. The electrode(s) 8 may be fabricated from elastic or superelastic materials so they can be deflected upon exposure to an external force (e.g. actuation of the vacuum, manual bending, etc.), or be treated so the electrode(s) 8 is/are malleable so the operator may tailor the electrode(s) to the anatomic structures. Similarly, the shaft 4, described above, may be treated so it is malleable.

The injection/support tube 100 can serve multiple functions. The injection/support tube 100 may be fabricated from a malleable metal or alloy to enable the operator to impart a shape to the electrode 8 and/or shaft 4 and maintain that shape during placement and/or coagulation. Alternatively, the injection/support tube 100 may be fabricated from a polymer tube or a braided polymer tube, or be embedded into the covering/insulation using an injection molding or extrusion process that defines a separate lumen (not shown). In this configuration, stylettes having discrete shapes and/or malleability may be inserted through the injection/support tube 100 to adjust the shape of the probe during placement or coagulation. This feature is especially relevant during less invasive access to the heart. The injection/support tube 100 incorporates apertures or cut-outs along the distal end 26 and is routed to a port (not shown) at the handle 102 of the probe to enable passive fluid cooling of the tissue during lesion creation. The suction force applied by a vacuum source (not shown) through the shaft lumen 6 pulls fluid (e.g. saline, Ringer's solution, plasmalite, etc.) from a fluid source (e.g. saline bag) through the injection/support tube 100 past the distal apertures or cut-outs 26 and along the lumen 6 of the probe conducting heat away from the soft tissue surface directly engaged against the electrode 8 using the vacuum. The known diameter and length of the injection/support tube 100 combined with the known pressure applied through the probe (preferably −400 mmHg) produce a constant fluid injection through the probe without the need for a separate pump/injector.

Figure 2A:
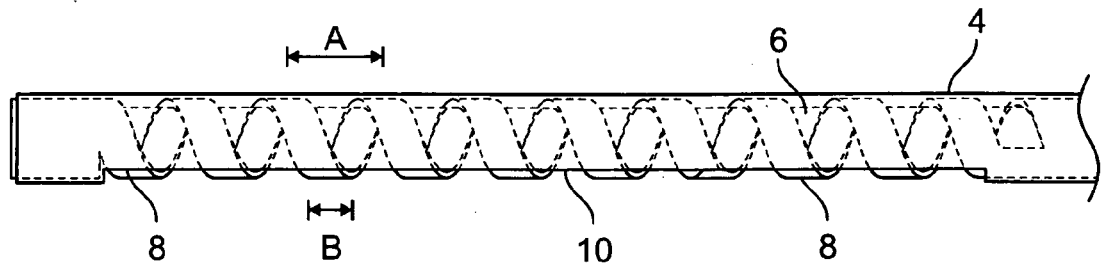
FIGS. 2A to 2C show a side view, a perspective view, and a bottom view of the distal section of an integrated vacuum coagulation probe embodiment.
Figure 2C:
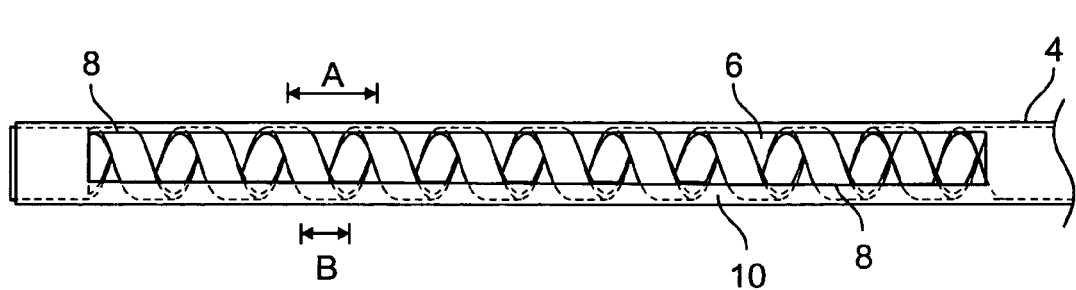
Figure 2D:
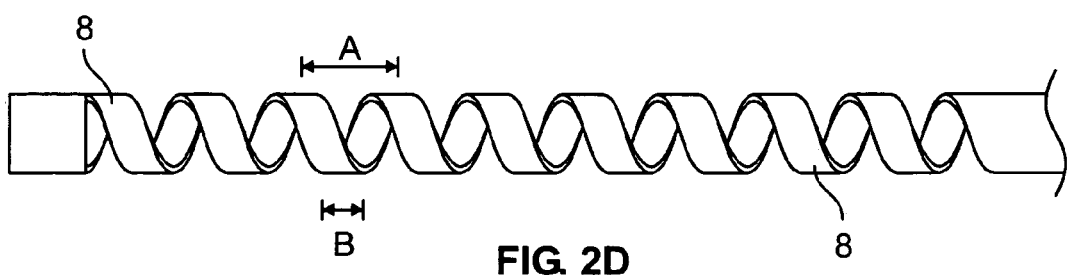
FIGS. 2D and 2E show bottom views of the electrode and covering components of the vacuum coagulation probe embodiment in FIGS. 2A to 2C.
Figure 2E:
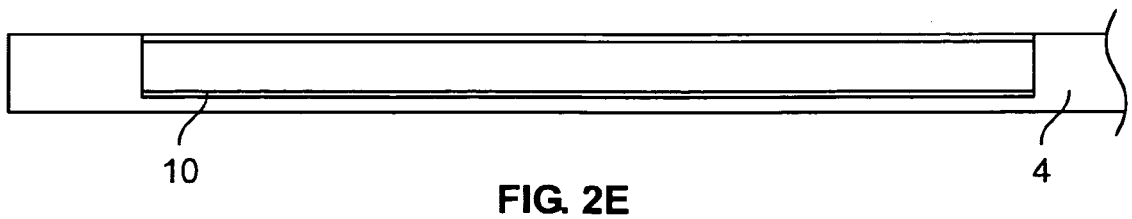
Figure 2B:
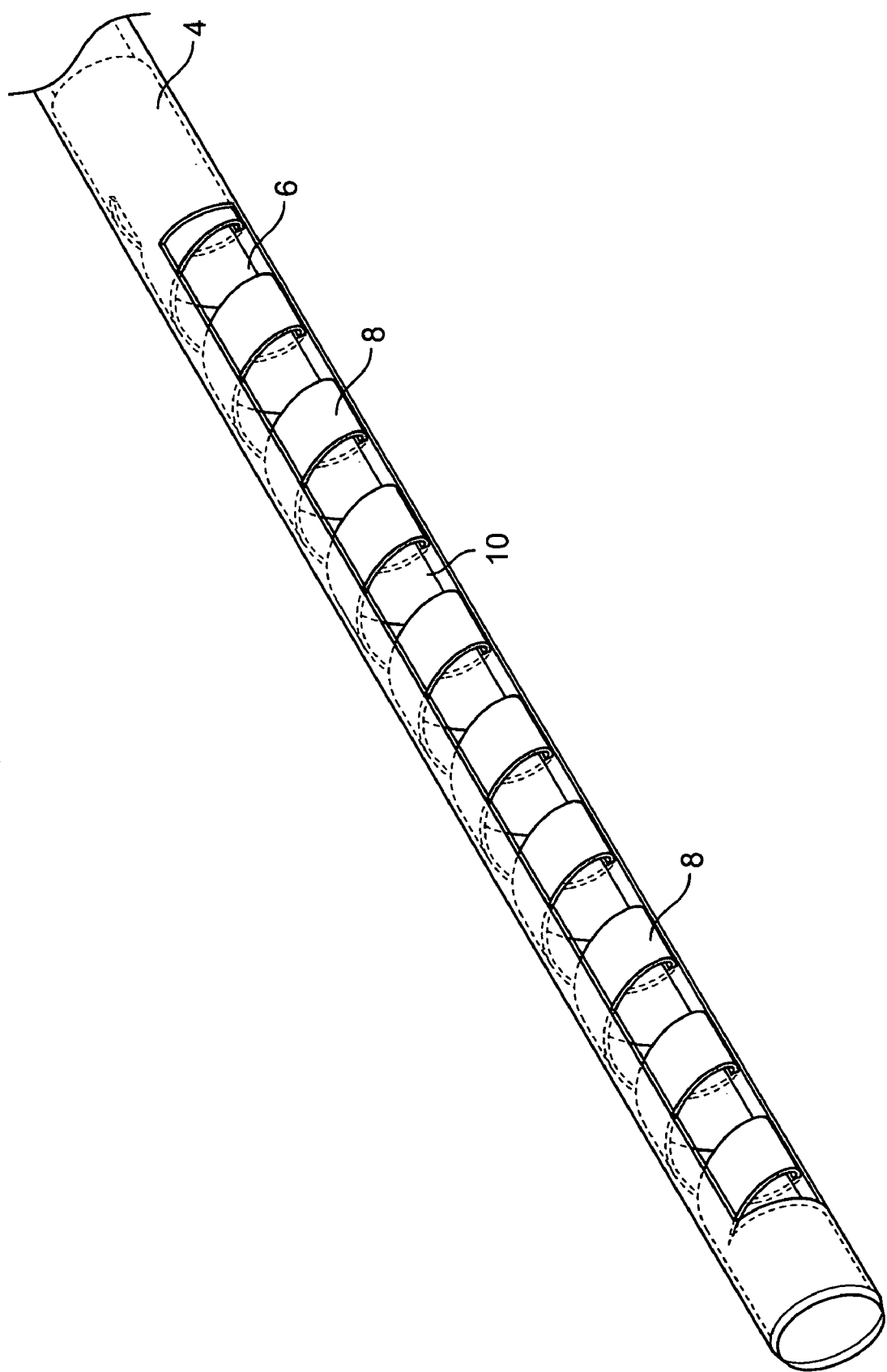

FIGS. 2A to 2C show the distal section of another vacuum coagulation probe embodiment used to coagulate soft tissue during open surgical and/or minimally invasive access (e.g. thoracoscopic, endoscopic, arthroscopic, laparoscopic, or other approach) into the body cavity. FIGS. 2D and 2E show two components (the electrode 8 and the covering or insulation over the electrode) of the vacuum coagulation probe in FIGS. 2A to 2C. FIG. 2D shows the cut tube that defines the electrode 8 and in this configuration the support of the shaft 4 with a lumen 6 therethrough. FIG. 2E shows the covering/insulation that covers the cut tube and incorporates an opening 10 that defines the electrode 8. The covering/insulation extends along the shaft 4 of the probe and terminates at the handle (not shown).

The integrated vacuum coagulation probe 2 embodiment in FIGS. 2A to 2E incorporates a flexible polymer shaft 4 that has a side wall, and covers or encapsulates an electrode 8 fabricated from a cut (laser cut, waterjet cut, chemically etched, etc.) tube (e.g. metal or alloy). The cut tube incorporates an unbroken distal tip extending into helical windings having a pitch (A) and width (B). The pitch (A) is the center-to-center distance between windings. The windings extend a length coincident with the electrode 8 that is defined by exposing the conductive surface of the electrode windings to tissue by at least one opening 10 in the side wall of the covering/insulation of the shaft 4. The cut tube may extend further beyond the at least one opening 10 that defines the at least one electrode 8 such that it continues along the entire shaft terminating at the handle attachment point. Alternatively, the cut tube may be limited to the electrode 8 region and terminate just past the opening 10 of the covering/insulation; this dedicated cut tube electrode 8 is then secured to a separate shaft 4. Preferably the inner diameter of the shaft is greater than or equal to the inner diameter of the electrode region to optimize the suction force applied along the opening and prevent tissue that is pulled into the electrode lumen from lodging in the shaft lumen. In the continuous cut tube (integral electrode and shaft) configuration, the electrode and shaft sections of the cut tube are covered or encapsulated by an insulative polymer with an opening 10 in the side wall of the polymer covering to define the electrode 8. The cut tube in this configuration may incorporate a single pattern of windings or adjust the pitch, winding width, and/or cut tube geometry from the electrode 8 region to the shaft region. In the separate electrode and shaft configuration, the covering/insulation along the electrode section may be integral with the shaft 4 covering/insulation or may comprise separate polymer coverings or insulations secured to the electrode 8 and the shaft 4.

The pitch (A) between individual windings defines the open space for tissue to be urged into the lumen 6 of the probe and into contact with the conductive windings by the external force of the suction originating from a vacuum source. The pitch (A) must be greater than or equal to 2 times the winding width (B) and is preferably greater than or equal to 4 times the winding width (B) to optimize the efficiency of engaging tissue to the electrode via the suction. In a representative embodiment, the pitch of the probe was 0.160", the winding width was 0.040", the width of the electrode defined by the width of the opening was 0.120", and the length of the electrode defined by the opening was 1.5". The probe was able to consistently create transmural, continuous lesions in soft tissue spanning the length of the electrode and having a depth greater than the width of the opening. In addition, no hot spots were observed and the lesions demonstrated consistent tissue damage throughout the lengths. This is dramatically different to non-suction based approaches that observe hot spots in regions of intimate contact and shallow lesions in regions of lesser tissue contact.

The principle factor in the improvement in the lesion creation capability observed in these integrated vacuum probe embodiments is the integration between the electrode and the vacuum mechanism. In the embodiments of the invention, the vacuum source applies suction to soft tissue directly in contact with the electrode; as opposed to inferior approaches, which incorporate independent suction means and electrode supports where suction is applied to tissue adjacent to tissue that contacts the electrode. By applying suction to soft tissue directly contacting the electrode, the soft tissue compresses into engagement with the electrode throughout the length consistently. The pitch (A) and winding width (B) are tailored so the probe electrode 8 contacts the compressed soft tissue at spaced intervals (either consistent or varied) thereby optimizing the current density profile along the length of the electrode and reducing the disparity in current density observed throughout the length of the conventional ablation probe electrodes. These factors enable the embodiments of the invention to create consistent lesions having defined dimensions without the need for several lesion monitoring tools (e.g. temperature sensors, etc.).

FIGS. 3A and 3B show an alternative cut tube embodiment that, along with the covering/insulation and corresponding opening(s) 10 therethrough, comprises the electrode 8 of the probe. If the cut tube further extends significantly beyond the opening(s) 10, then it may also comprise the shaft 4 of the probe. This electrode 8 embodiment comprises multiple windings that emanate from an axial backbone. The windings have at least one pitch (A) and at least one width (B).

FIGS. 4A to 4D show a multilumen integrated vacuum probe configuration in which a first electrode 8 is offset from the tissue surface and a second electrode 108 may be incorporated to enable bipolar energy transmission between the first and second electrodes.

Figure 4A:
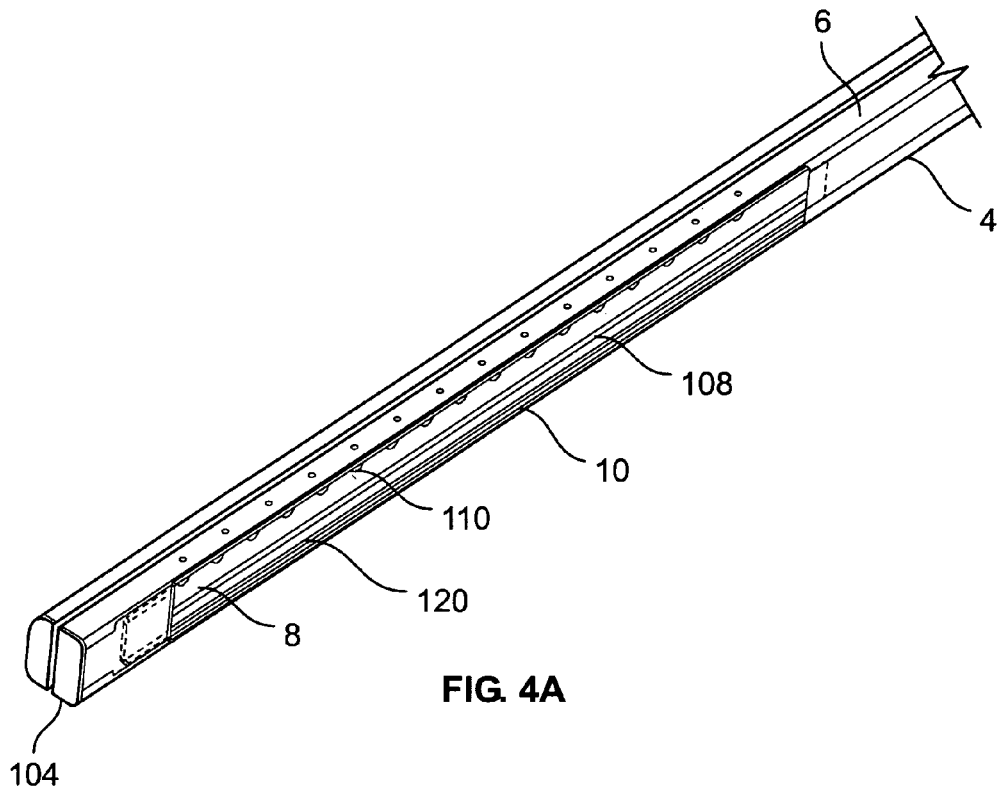
FIGS. 4A to 4D show a perspective view, a bottom view, a side view, and a cross-sectional view of an integrated vacuum coagulation probe embodiment that incorporates an offset between the active electrode and the surface of the probe, and multiple lumens for injection of cooling or therapeutic media.
Figure 4B:
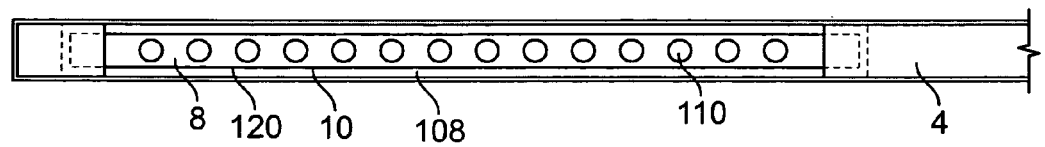
Figure 4C:
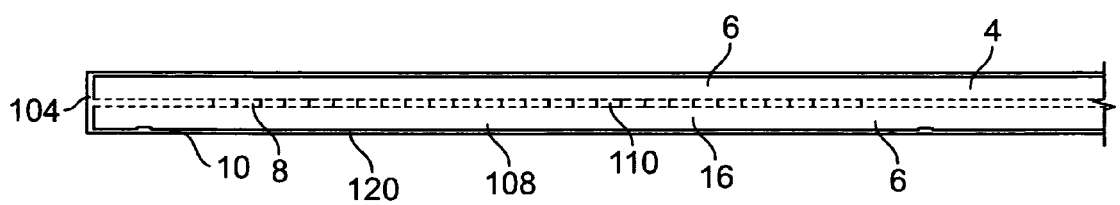
Figure 4D:
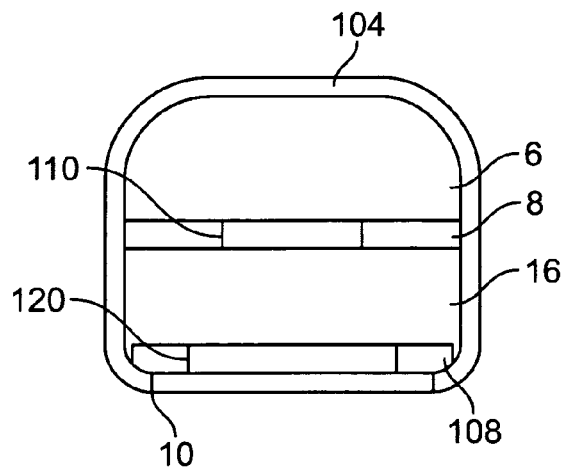

As shown in FIGS. 4A to 4D, the probe consists of a dual lumen tubing fabricated from a non-conductive polymer extruded or injection molded into the dual lumen tubing having a side wall with openings 10, a distal tip 104 that caps the distal end of the lumens 6 and 16, and a first electrode 8 and a second electrode 108 secured to the side wall of the dual lumen tubing. The at least one first electrode 8 is secured to the side wall of the probe offset from the opening 10 through the side wall. The first electrode(s) 8 comprise at least one pore or opening 110 coupled to the first lumen 6 of the multilumen tubing, as shown in FIGS. 4B and 4D. The at least one second electrode 108 is attached to the side wall at the side wall opening 10 and itself comprises at least one opening 120. The electrode 8 and 108 embodiments in FIGS. 4A to 4D may consist of lengths of sheet or bar material, having predetermined wall thicknesses, secured to the multi-lumen shaft tubing. The electrodes may fit inside notches created in the shaft tubing that houses the electrodes, adhesively bonded to openings in the shaft, ultrasonically welded to openings in the shaft, laser welded, spot welded or secured to the shaft with other processes, depending on the materials used for the electrodes and the shaft. Alternatively, the electrodes and the shaft may be fabricated from a single length of conductive tubing (e.g. single lumen or multi-lumen), or less conductive tubing deposited or otherwise covered with a metallic coating. In these cases, the shaft region of the probe is covered with an insulative material to isolate the shaft from the electrode(s). In another embodiment at least one of the electrodes 8 and 108 comprise helical coils or other flexible wire pattern bonded to the side wall of the probe.

As shown in FIGS. 4A to 4D, lumen 16 defined by the multi-lumen tubing routes a fluid injection port (not shown) at the handle, through the shaft 4, along the electrodes 8 and 108 and to the electrode section of the vacuum coagulation probe 2 to enable fluid cooling of soft tissue contacting the electrodes 8 and 108. This fluid then flows through opening 110 through electrode 8 and passes through the suction lumen 6, past the suction port (not shown) and into a vacuum reservoir. Injection of fluid through the multilumen vacuum probe enables cooling soft tissue during coagulation to enable transmitting more energy into the soft tissue thereby conducting the heat further into the tissue and creating deeper lesions.

This integrated, multilumen vacuum probe embodiment enables directly heating unwanted tissue superficial to healthy tissue that needs to be preserved (e.g. articular cartilage removal without damaging the underlying bone cells). The offset of electrode 8 from the soft tissue surface and the passive injection of cooling fluid provides a buffer from which only tissue urged into contact via the suction is heated and removed without conducting heat deeply into the underlying tissue. As such articular cartilage may be heated and removed while preserving the bony cells.

In another application, the multilumen vacuum probe may inject therapeutic, pharmacologic solutions (e.g. gludaraldehyde, other cross-linking agents, ethanol, heparin, rapamycin, paclitaxel, or other drug) through the fluid injection lumen 16 and into contact only with tissue engaged at opening 10 via the vacuum. As such, toxic substances such as gludaraldehyde may be used to invoke a tissue response and quickly removed without adversely affecting adjacent anatomy. As such the vacuum probe may cause tissue shrinkage by engaging tendons, or other soft tissue with a therapeutic cross-linking agent that is removed after exposing only a specific region of tissue. Alternatively, drug solutions may be locally transmitted to specific tissue regions to kill cells, alter cellular structure, prevent a biological reaction, or other purpose. The isolated injection of therapeutic solutions may be augmented by the delivery of RF energy (continuous or pulses) to cause electroporation or other tissue response to augment the impact of the therapeutic solution injection.

The embodiments described above may be treated so they are malleable and may be deformed into a desired shape required to access the desired coagulation location and/or create the desired lesion length, and shape. An alternative approach, not shown in the Figures, is to incorporate a steering mechanism in the vacuum coagulation probe. The steering mechanism may be used to deflect the entire electrode relative to the shaft and/or a portion of the electrode. At least one pull-wire can be secured to the electrode at the electrode to shaft junction if the electrode is to be deflected as a unit relative to the shaft, or along the electrode up to the distal end of the probe if the electrode is to be deflected. The opposite end of the pull-wire(s) are routed to the handle where it is secured to an actuation knob, not shown, to manually deflect the vacuum coagulation probe into a curve. The curve shape, angle and radius is defined by the distance along or from the electrode(s) at which the pull-wire(s) is/are secured and the stiffness relationship between the shaft and the electrode(s). A guide-coil or other radially restraining component can be housed around the pull-wire(s) in the shaft to specify the stiffness of the shaft and further define the radius of curvature and angle of deflection of the distal region of the probe as the pull-wires are actuated.

Figure 5A:
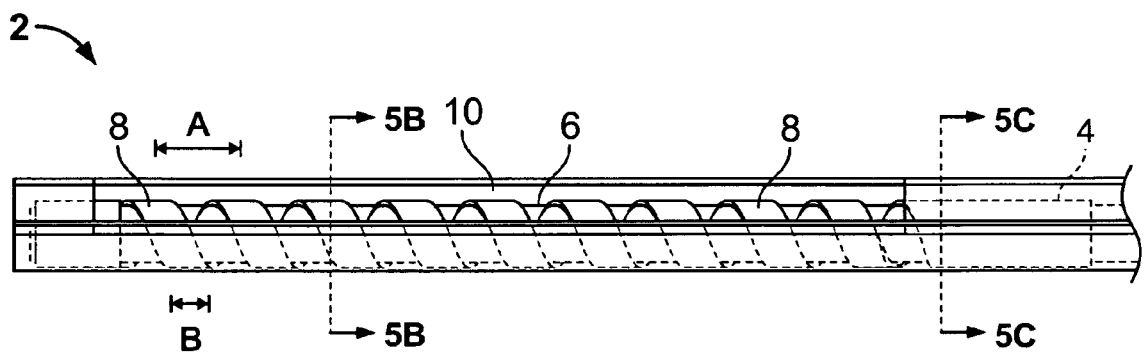
FIGS. 5A to 5C show a side view, and cross-sectional views taken along A-A and B-B of an integrated vacuum coagulation probe embodiment incorporating an offset between the electrode and the tissue engaging opening.
Figure 5B:
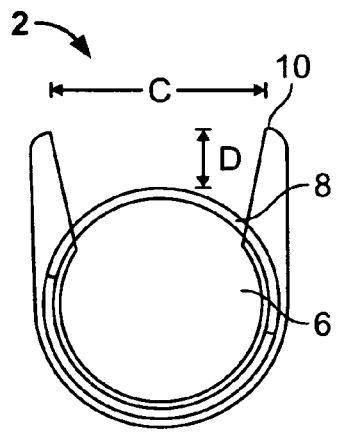
Figure 5C:
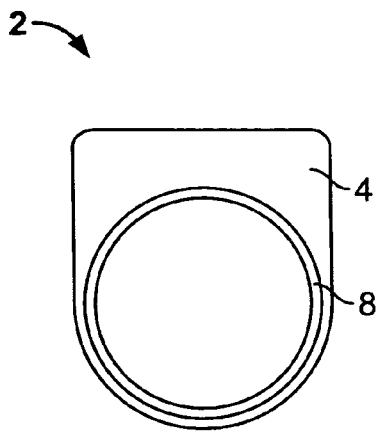

FIGS. 5A to 5C show the distal section of another integrated vacuum coagulation probe 2 embodiment. This probe 2 incorporates at least one electrode 8 fabricated as a series of windings from a cut tube or wound coil having at least one pitch (A) and at least one winding width (B). The cut tube defines a lumen 6 for providing a suction path from a vacuum source at the handle (not shown). A polymer covering/insulation is extruded, injection molded, or dipped over the cut tube to preserve the lumen 6 and provide at least one isolated opening 10 inside which the conductive windings/elements of the electrode 8 are exposed (as shown in FIG. 5B as a blackened section of the conductive windings). The proximal region of the polymer covered cut tube defines the shaft 4. As shown in FIG. 5B, the tissue contacting surface of the covering/insulation along the opening 10 is offset from the electrode 8 by a distance (D). As such, the side wall of the covering/insulation is thicker along the opening 10, defined by the offset (D), than 180 degrees to the opening 10. The opening 10 also comprises a width (C) into which soft tissue is directly urged into engagement with the at least one electrode 8 via suction.

The ratio between the offset (D) and the width (C) produces a coagulation response dependent on the application. For direct soft tissue coagulation, such as required during atrial fibrillation ablation or tendon shrinkage, C>2D to maximize the contact between uneven or creased soft tissue surfaces and the exposed conductive surface of the electrode winding(s). However, D is always >0 (e.g. the covering/insulation extends beyond the at least one electrode) to enhance the suction response of the vacuum coagulation probe.

By incorporating an offset with a flexible polymer covering/insulator the ability for the vacuum coagulation probe to contact soft tissue and produce a vacuum seal required to engage the soft tissue and bring it into engagement with the at least one electrode 8 is dramatically improved. This is especially important in applications where the soft tissue surface is creased or uneven. The flexible covering/insulation essentially forms an extension about the at least one opening 10 that fills the creases or uneven anomalies thereby preserving the suction force of the soft tissue to the vacuum probe and ensuring the entire length of soft tissue engages the at least one electrode 8.

In addition, this offset also lifts the tissue layer separating it from underlying tissue layers. For example, during tendon shrinking applications of the shoulder, the tendon is engaged against the at least one electrode via the suction and is lifted from underlying nerves, or blood vessels thereby directly heating the tendon tissue while preserving the integrity and functionality of the underlying nerves and blood vessels. This feature is also important during atrial fibrillation ablation where underlying vessels such as the circumflex artery, the right coronary artery, and the coronary sinus reside in the interatrial groove. When coagulating tissue completely to the valve annulus to use the annulus as a barrier to electrical wavelet propagation, soft tissue along the interatrial groove is coagulated. By lifting the atrial tissue along the interatrial groove and cooling underlying tissue layers, the atrium is coagulated up to the interatrial groove yet the underlying blood vessels are preserved.

For applications where the target tissue that the operator wants to heat resides between a definite soft tissue surface that needs to be preserved and the electrode, a greater offset (D) is incorporated into the vacuum coagulation probe. Even so, C>D. This configuration addresses articular cartilage removal where jagged cartilage above the bony surface is heated and removed via the vacuum without thermally damaging the underlying bony surface. The integrated electrode 8 and vacuum transmission of the vacuum coagulation probe embodiments of the invention enable directly heating the target tissue by pulling the target tissue into engagement with the edges of the electrode 8. The fluid injection mechanism enables cooling underlying tissue that is offset from the electrode to preserve that soft tissue layer while evoking the desired effect on the contacted tissue layer.

Figure 6A:
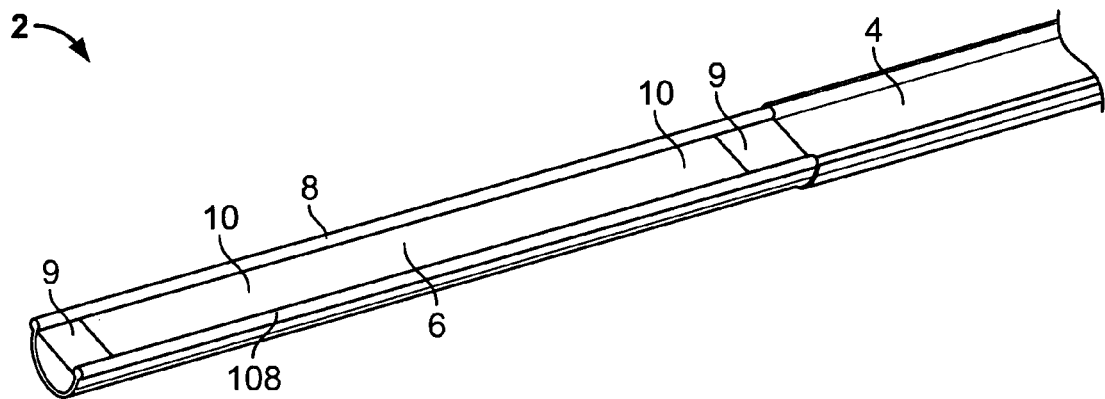
FIGS. 6A and 6B show perspective views of two non-integrated vacuum coagulation probe embodiments incorporating electrodes adjacent the tissue engaging opening.
Figure 6B:
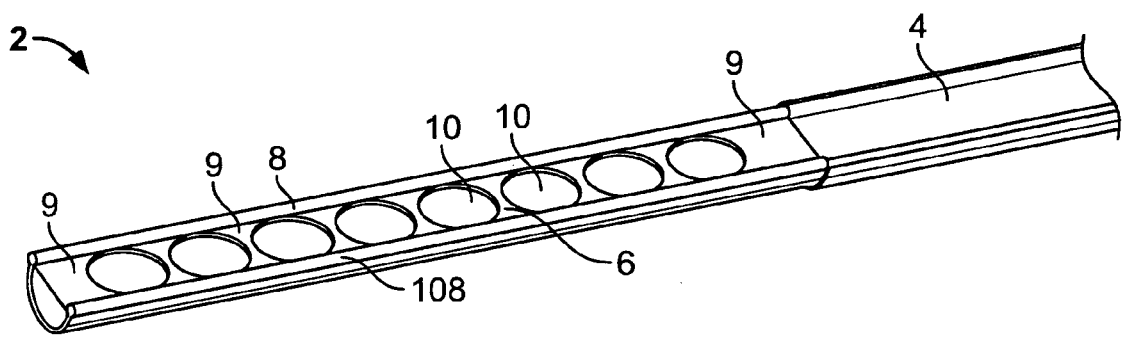

FIGS. 6A and 6B show two NON-integrated vacuum coagulation probe embodiments where the electrodes 8 and 108 comprise two rods oriented adjacent to the vacuum opening 10 of the covering/insulation 9. In the embodiment in FIG. 6A, a single slot defines the opening 10 between the adjacently oriented electrodes 8. In the embodiment in FIG. 6B, a series of pores 10 define the suction pores through the probe. In these embodiments the suction applies vacuum to the insulative covering 9 such that the soft tissue will engage the adjacent electrodes.

These NON-integrated embodiments enable transmitting RF energy in bipolar mode between the adjacent electrodes 8 and 108. The electrodes' close proximity to the suction opening(s) 10 in the embodiments of FIGS. 6A and 6B enable contacting the soft tissue to the adjacent electrodes indirectly but the location of the electrodes being adjacent to the suction source opening(s) 10 limit the probes' ability to provide the flexibility required to engage soft tissue throughout the length of the electrode unless the soft tissue surface is extremely smooth. In addition, these probe embodiments in FIGS. 6A and 6B, where the electrodes' are located adjacent to the suction opening(s) 10, are not able to readily be oriented into 3-dimensional patterns (e.g. curves where the probe electrodes' are bent into at least one radius of curvature) while preserving the ability to reliably engage the soft tissue to the openings. As such their ability to reliably create consistent, transmural lesions throughout the entire length of the electrode(s) is impaired when compared to the integrated probe embodiments (FIGS. 1A to 1C, 2A to 2E, 3A to 3B, 4A to 4D, and 5A to 5C.). As such, applications such as atrial fibrillation, where the tissue surface is uneven and the 3-dimensional anatomic profiles of the atria, require the more flexible and tailored electrodes that integrate the vacuum features with the electrode as described in FIGS. 1A to 5C above.

However, the embodiments in FIGS. 6A and 6B where the electrodes are adjacent to the vacuum opening(s) are suitable for planar tissue surfaces that don't require precise, direct tissue coagulation. The further adjacent electrodes are separated from the vacuum opening(s), the device's flexibility, ability to completely engage 3-dimensional tissue structures, and the lesion creation reliability are significantly degraded. In fact, adjacent electrodes that are laterally spaced away from the vacuum openings are unable to be bent into the required shapes to coagulate transmural, continuous lesions capable of treating atrial fibrillation.

Existing atrial fibrillation coagulation or other soft tissue coagulation treatment applications performed thoracoscopically, endoscopically, arthroscopically, laparoscopically, or with other less invasive approach tend to create incomplete curvilinear lesions because the desired lesion sites are inaccessible, contact to the tissue is poor, and the temperature gradient from the contacted tissue surface to the opposite tissue surface is dramatic; these conditions limit the creation of continuous, transmural, curvilinear, lesions. This is especially the case when blood is flowing along the opposite tissue surface producing a heat sink that cools that tissue surface further affecting the temperature gradient and limiting the lesion depth. As such, the existing techniques can be inferior and have a higher rate of arrhythmia persistence than the vacuum coagulation probe devices of the invention.

In addition, incomplete lesions during atrial fibrillation treatment have been demonstrated to generate substrates for persistent atrial flutter and/or atrial tachycardia. For some other applications, the inability to create consistent and complete lesions allows cancerous cells, or other disease substrates to prevail. For applications such as tendon shrinkage or articular cartilage removal, the inability to direct coagulation to a specific region of tissue without affecting underlying layers of tissue indiscriminately damages tissue structures (e.g. nerves, blood vessels, bone cells, or other untargeted tissue) that need to be preserved. The same concern holds true for atrial fibrillation ablation in which lesions extend to the interatrial groove where the circumflex, right coronary artery, and coronary sinus reside near the valve annulus and must be preserved. The embodiments of the invention mitigate these risks by engaging isolated, target tissue regions and enabling direct coagulation of a specific region of tissue without damaging unwanted tissue structures.

Figure 7:
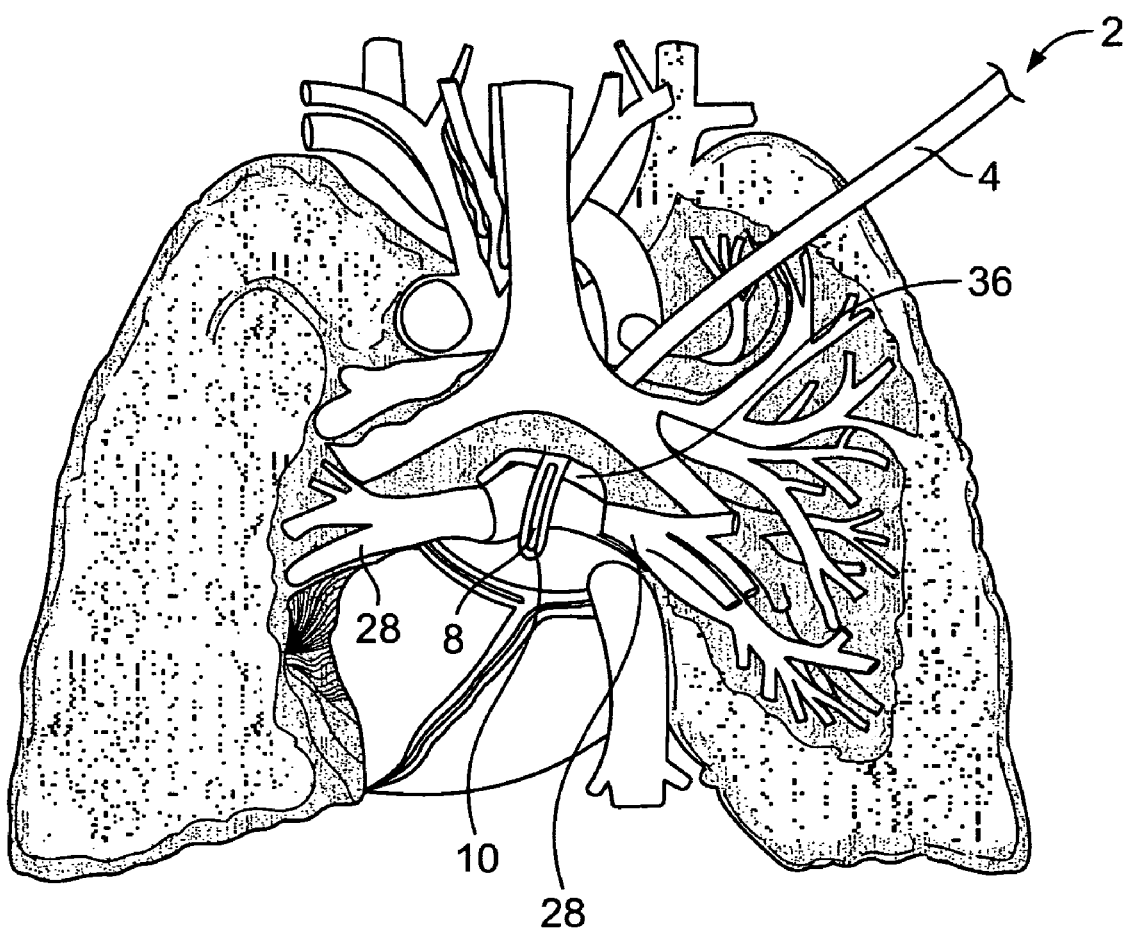
FIG. 7 shows a posterior view of a heart and associated vasculature with a vacuum coagulation probe embodiment placed to access regions of the left atrium about the pulmonary veins.
Figure 8:
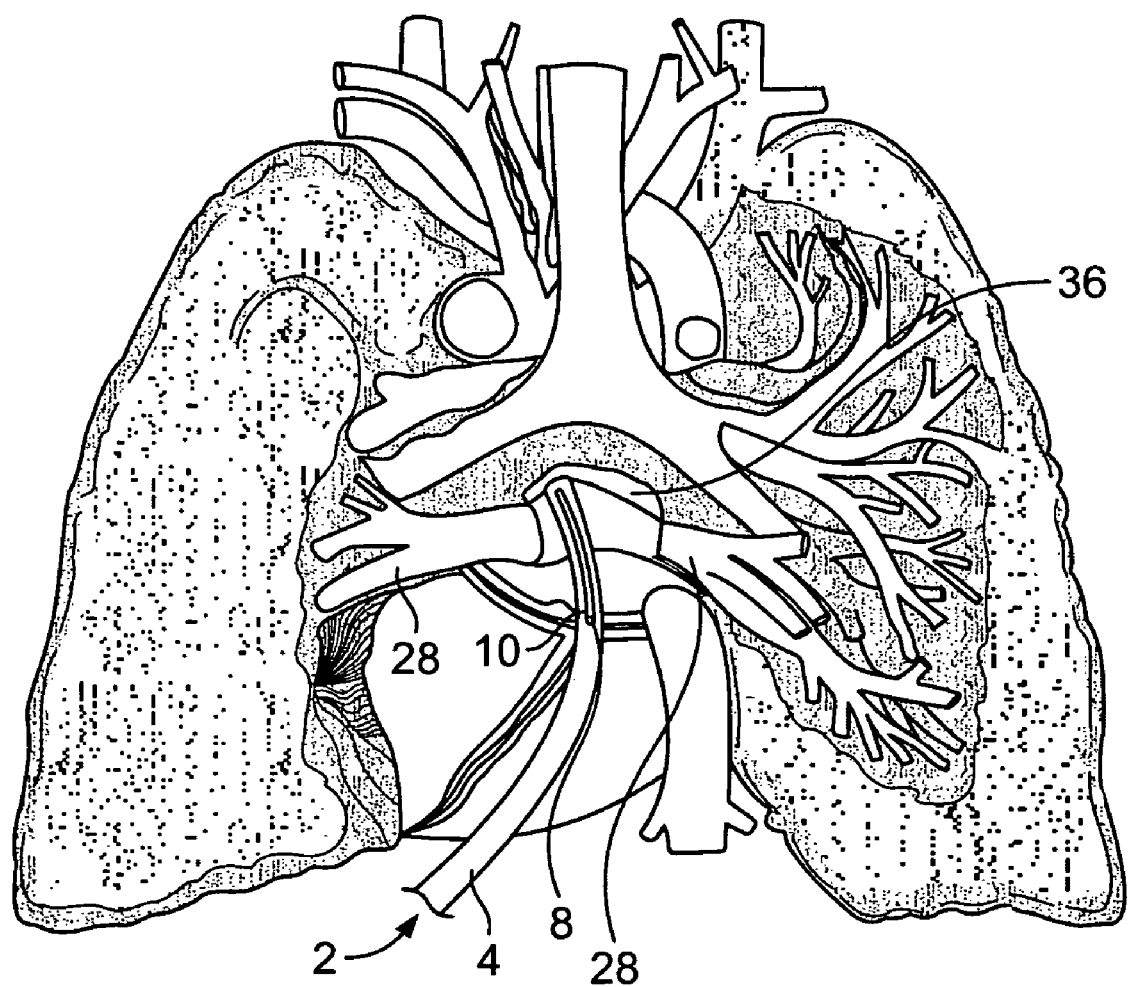
FIG. 8 shows a posterior view of a heart and associated vasculature with a vacuum coagulation probe embodiment placed to access regions of the left atrium about the pulmonary veins.

An approach for treating atrial fibrillation with the vacuum coagulation probe 2 of the invention is shown in FIGS. 7 and 8. The probe is inserted into the thoracic cavity through ports placed in intercostal spaces, a thoracotomy, a thoracostomy, a median sternotomy, a mini-sternotomy, a xiphoid access port, a lateral subthoracic access site, or other less invasive surgical procedure. As such, the shaft 4 of the probe has a low profile to facilitate advancing through small cavities associated with limited access applications. The probe 2 may be deflected or deformed into the desired lesion pattern, which in FIGS. 7 and 8 comprise slight curves passing between the left and right pulmonary veins 28. Once placed, the vacuum source is actuated to apply a suction force through the vacuum opening(s) 10 to urge the epicardium of the left atrium 36 into intimate contact with the electrode(s) 8. It should be noted that the vacuum coagulation probe can instead be placed against the endocardium of the atria during cardiopulmonary bypass procedures where the atria are open for valve (mitral, tricuspid, and/or atrioventricular) repair or replacement procedures or beating heart procedures where an introducer into the atrium is obtained through an atrial appendage, the atrial free wall, the ventricle, a pulmonary vein, a vena cava, or other conduit that may be closed upon completion of the coagulation procedure.

It should be noted that any pattern of curvilinear, transmural lesions may be created along the epicardial surface or the endocardial surface with the vacuum coagulation probe embodiments of the invention. Other potential lesion patterns capable of treating atrial fibrillation, which the vacuum coagulation probe may replicate, are described in U.S. Pat. No. 6,071,279 entitled "Branched structures for supporting multiple electrode elements" and incorporated herein by reference.

The entire length of the exposed electrode(s) is used to apply suction through the at least one opening 10 to apply a vacuum force against the epicardium (or endocardium) and urge the tissue into engagement with the electrode(s).

Then radiofrequency (or d.c.) energy is transmitted to the electrode(s) in unipolar or bipolar mode such that the current density is transmitted into tissue adjacent the at least one electrode and ohmic heating causes the tissue adjacent the at least one electrode to heat and conduct the heat further into depths of tissue. Alternatively, the electrode(s) may be fabricated from a resistive element (e.g. tantalum, tungsten, etc.) in which radiofrequency (or d.c.) energy applied along the resistive element, between wire connections at opposite ends of the resistive element, heats the element and the intimate tissue to electrode(s) contact enables thermal conduction of the heat from the electrode into the target soft tissue.

The transmission of energy in unipolar or bipolar mode causes the soft tissue to heat which conducts further into adjacent soft tissue; alternatively the heating of a resistive element causes the resistive electrode(s) to heat which is then conducted into adjacent, contacted soft tissue. As cardiac cells (and any muscle tissue) are heated above 50° C., irreversible conduction block occurs and the cells become non-viable (Nath, et al. Cellular electrophysiologic effects of hyperthermia, on isolated guinea pig papillary muscle: implications for catheter ablation. Circulation. 1993; 88:1826-1831). As such, a consistent, continuous length of atrial tissue extending from the epicardial surface to the endocardial surface must be heated above 50° C. to treat atrial fibrillation.

For other applications involving coagulation of soft tissue to shrink collagen rich tissues or prevent shrinking of collagen tissues, heating of the soft tissue must be controlled, which the vacuum coagulation probe embodiments of the invention enable. Published studies evaluating the response of vessels (arteries and veins) to heat have focused on the ability to permanently occlude vessels. Veins have been shown to shrink to a fraction of their baseline diameter, up to and including complete occlusion, at temperatures greater than 70° C. for 16 seconds; the contraction of arteries was significantly less than that of veins but arteries still contracted to approximately one half of their baseline diameter when exposed to 90° C. for 16 seconds (Gorisch et al. Heat-induced contraction of blood vessels. Lasers in Surgery and Medicine. 2: 1-13, 1982; Cragg et al. Endovascular diathermic vessel occlusion. Radiology. 144: 303-308, 1982). Gorisch et al explained the observed vessel shrinkage response "as a radial compression of the vessel lumen due to a thermal shrinkage of circumferentially arranged collagen fiber bundles". These collagen fibrils were observed to denature, thus shrink, in response to heat causing the collagen fibrils to lose the cross-striation patterns and swell into an amorphous mass.

Embodiments of the invention prevent or limit the heat-induced contraction of such structures as the pulmonary veins by applying a vacuum force capable of maintaining the position (e.g. diameter) of the vessel while heating the soft tissue. As such, the vessel is stented or supported from the external surface as the tissue is heated above the required 50° C. threshold without concern that the vessel may accidentally become stenosed due to the heat-induced contraction.

Alternatively, the vacuum coagulation probe embodiments direct heat-induced contraction of such structures as tendons, ligaments, skin or other anatomy in which the therapy is designed to heat thereby denature the collagen and shrink the tissue until the desired shape or effect is achieved. In addition, the vacuum coagulation probe can reposition the soft tissue while heat is applied to the soft tissue to direct the shrinking and cause the collagen fibrils to reorganize reforming the soft tissue into a desired shape.

Figure 9:
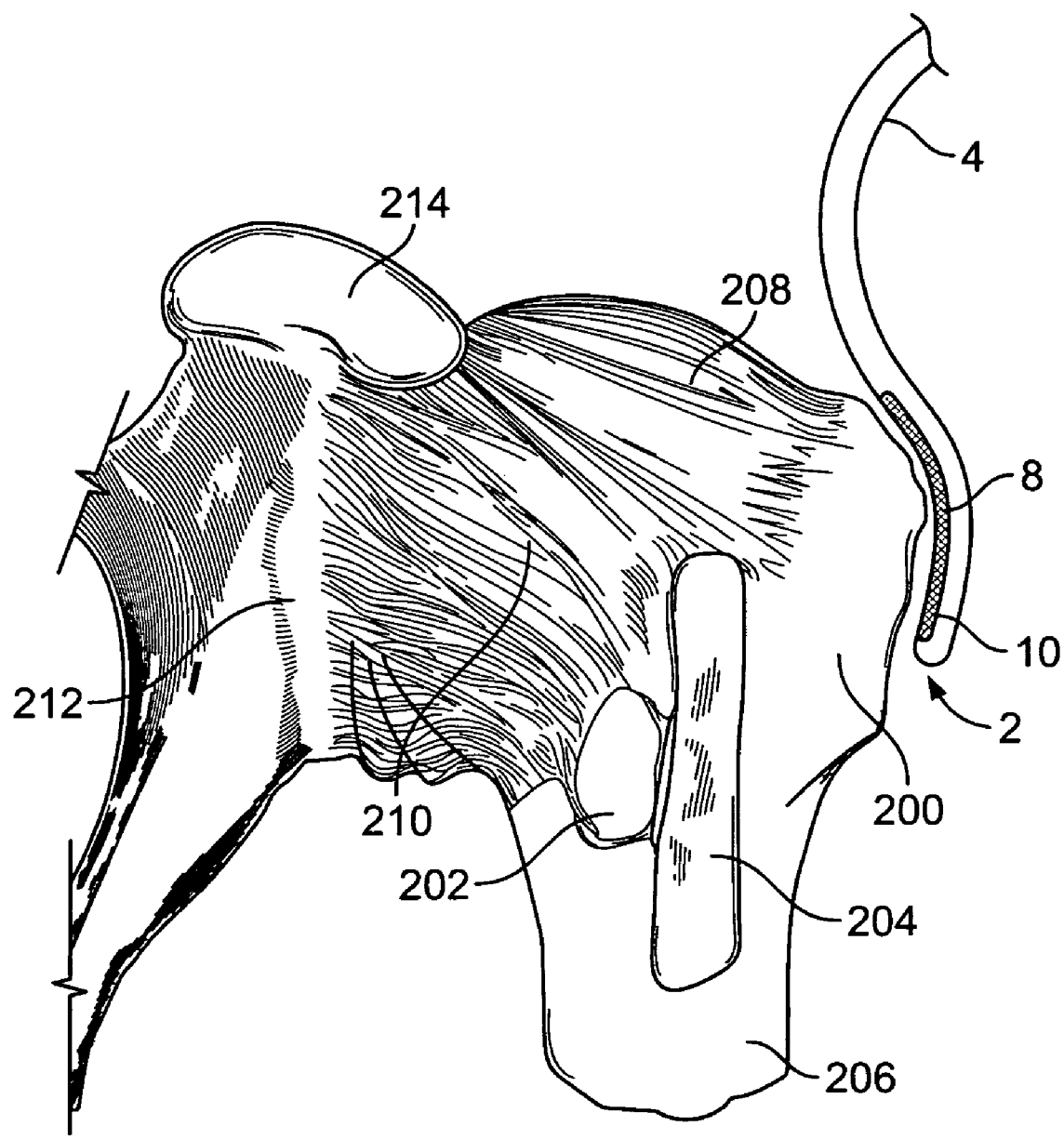
FIG. 9 shows a front view of a shoulder and associated anatomy with a vacuum coagulation probe embodiment placed to remove articular cartilage or unwanted tissue from the bony surface, or to coagulate stripes of tendon tissue to cause shrinkage and strengthening of the tendon.

FIG. 9 shows a shoulder with an integrated vacuum coagulation probe 2 embodiment placed along the bony surface, tendon, ligaments, muscles, or other tissue. As such the integrated vacuum coagulation probe may be used for articular cartilage removal, tendon or ligament shrinking, or other indications involving collagen or cellular modification of tissue structures.

The anatomy of the shoulder consists of the Greater Tubercle 200, the Tendon of Biceps 204, the Humcrus 206, the Lesser Tubercle 202, the Capsular Ligament 210, the Coraco-Humeral Ligament 208, the Coracoid Process 214, and the Neck of the Scapula 212

During articular cartilage removal, cartilage fragments are heated to soften their attachment to the bony cells and enable removal from the bone while preserving the integrity of the bony cells. As such the integrated vacuum coagulation probes in FIGS. 4A to 4D and 5A to 5C contain the electrode(s) 8 offset from the tissue contacting surface along the opening 10. As such only cartilage contacting the electrode(s) 8 is heated and removed via the vacuum while the underlying bony surface is cooled by fluid passively flowing along the fluid injection lumen 16.

During tendon or ligament shrinking/altering procedures, stripes of lesions are superficially created along the surface of the tendon without damaging underlying nerves or other anatomic structures. As such, integrated vacuum coagulation probes 2 of FIGS. 1A to 1C, and 2A to 2E are tailored to create a matrix of coagulated tissue defining a grid of coagulated tissue with viable tissue interspersed. As such the electrode(s) may be placed along the tendon to create sequential lines separated by widths of non-affected tissue. Alternatively, the pitch (A) to winding width (B) ratio may be substantially increased to create distinct lesion lines separated by non-heated tendon in the space between these widely separated windings. Either way the integrated vacuum coagulation probe is capable of creating a grid of coagulated tissue interspersed with non-heated tissue regions.

The integrated vacuum coagulation probe embodiments of FIGS. 4A to 4D and 5A to 5C can also be utilized in shrinking tendons, ligaments, or otherwise modifying such collagen-based tissue structures either by locally heating the target tissue layer as described above or transporting cross-linking agents (e.g. gludaraldehyde) or other pharmacological substances specifically to the region of soft tissue engaged against the opening 10 of the probe. As such these typically toxic materials are also removed after invoking their desired tissue response. Cross-linking agents have been demonstrated to cause collagen-induced shrinking of tissue structures and increase the strength of such structures; therefore, they are highly suited, despite their toxicity, to strengthening and shrinking damaged tendons. As such these integrated vacuum coagulation probe embodiments enable treated the tissue with such agents without concern for their toxicity since they are immediately removed by the vacuum.

The integrated vacuum coagulation probe embodiments of the invention also enables treating a tissue surface without damaging underlying tissue structures (e.g. nerves or vascular tissue) by slightly lifting the target tissue surface away from the underlying layers via the vacuum while coagulating the target tissue layer. As such, the underlying tissue is preserved.

Figure 10:
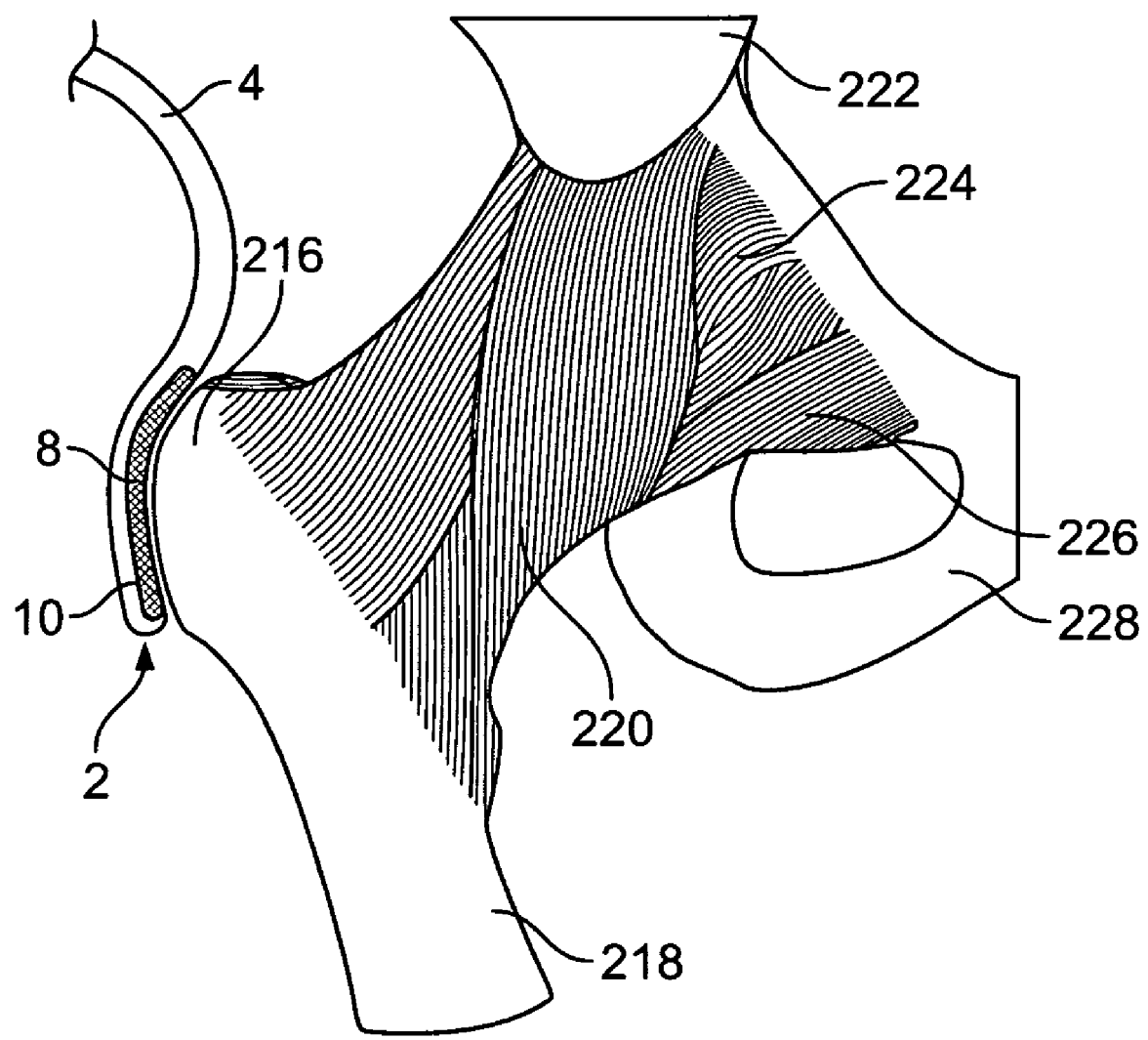
FIG. 10 shows a front view of a hip and associated anatomy with a vacuum coagulation probe embodiment placed to remove articular cartilage or unwanted tissue from the bony surface.

FIG. 10 shows a hip with a vacuum coagulation probe 2 embodiment placed to remove articular cartilage or shrink tendons, ligaments, muscle, or other soft tissue as described for the shoulder above. The hip anatomy shown in FIG. 10 consists of the Greater Trockanter 216, the Femur 218, the Iliofemoral Ligament 220, the Anterior inferior iliac spine 222, the Iliopectin Emin 224, the Pubo-capsular Ligament 226, and the Tuberosity of Ischium 228.

Figure 11:
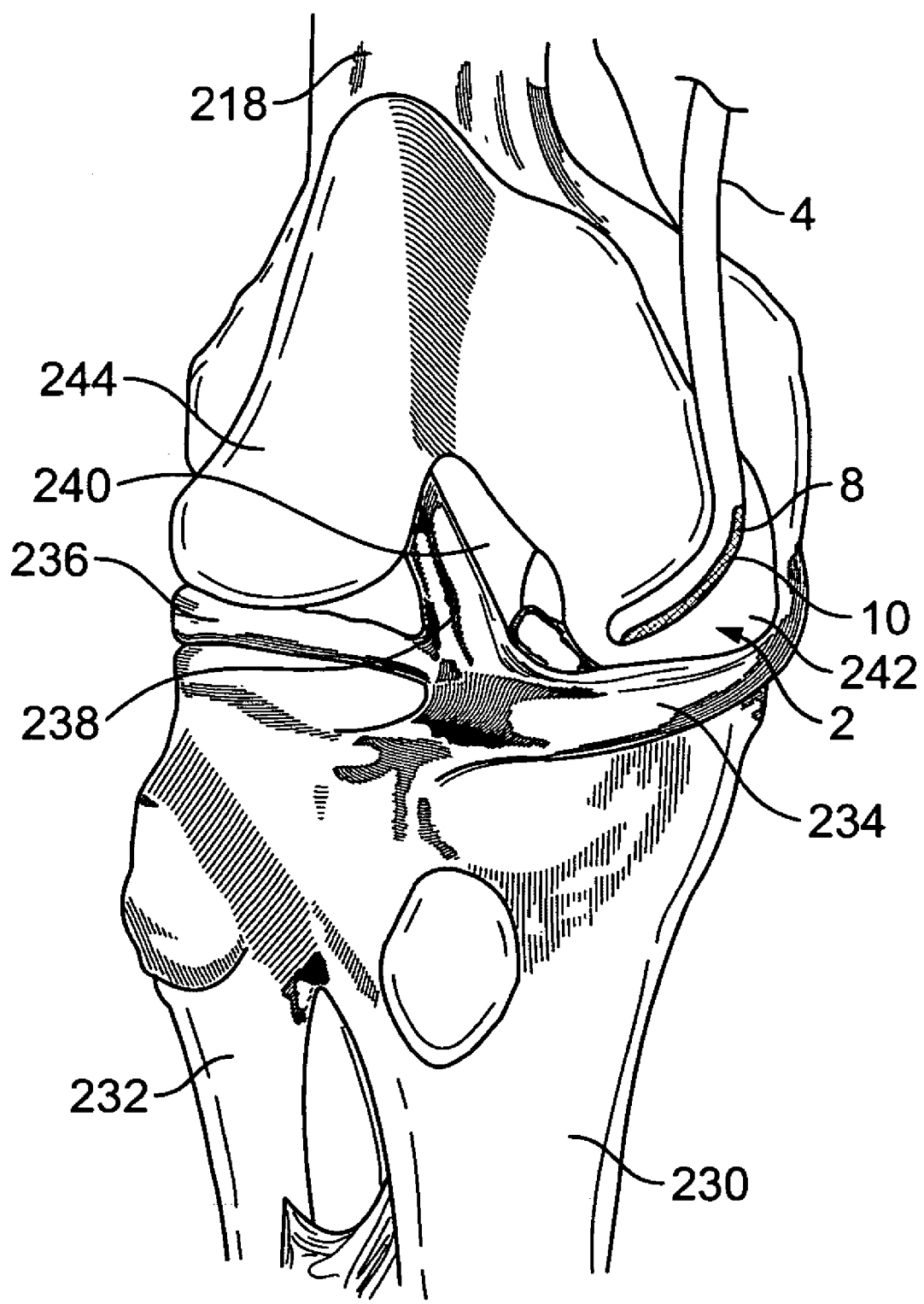
FIG. 11 shows a front view of a knee and associated anatomy with a vacuum coagulation probe embodiment placed to remove articular cartilage or unwanted tissue from the bony surface, or to coagulate stripes of tendon tissue to cause shrinkage and strengthening of the tendon.

FIG. 11 shows a knee with a vacuum coagulation probe 2 embodiment placed to remove articular cartilage or shrink tendons, ligaments, muscle, or other soft tissue as described for the shoulder above. The knee anatomy shown in FIG. 11 consists of the Femur 218, the Medial Condyle, 242, the Lateral Condyle 244, the Anterior Cruciate Ligament 238, the Posterior Cruciate Ligament 240, the Medial Meniscus 234, the Lateral Meniscus 236, the Tibia 230, and the Fibula 232.

The embodiments of the invention described in this specification can also be used for coagulating other soft tissues such as breast tissue, the liver, the prostate, gastrointestinal tissue, skin, or other soft tissue for the coagulation of cancerous cells; or other collagen based soft tissue for the heat induced shrinking or contraction.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

We claim:

1. A surgical device for coagulating soft tissue comprising:
a first elongate member comprising a side wall with at least one lumen and at least one conductive element attached to said side wall;
at least one opening through said side wall of said first elongate member, said opening coupled to said lumen and exposing said conductive element;
a flexible extension about the opening that is adapted to deform to sealingly engage the soft tissue;
wherein said conductive element comprises at least one helical winding having at least one pitch and at least one winding width; and
wherein a portion of the elongate member containing the conductive element and the conductive element are configured to deflect to conform to uneven surfaces of soft tissue, and where the conductive element is exposed only at said opening.

2. The device of claim 1, where the portion of the elongate member containing the conductive element and the conductive element are elastic.

3. The device of claim 1, where the elongate member containing the conductive element and the conductive element are malleable.

4. The device of claim 1, wherein said side wall comprises an insulator covering.

5. The device of claim 1, wherein said conductive element comprises a series of helical windings having at least one pitch and at least one winding width: wherein said pitch is greater than or equal to two times said width.

6. The device of claim 1, wherein said conductive element comprises a series of helical windings having at least one pitch and at least one winding width, wherein said pitch is greater than or equal to four times said width.

7. The device of claim 1, wherein the external surface of said side wall along said opening is offset from said conductive element by a distance; wherein the width of said opening is greater than or equal to said offset distance.

8. The device of claim 1, wherein the external surface of said side wall along said opening is offset from said conductive element by a distance; wherein the width of said opening is greater than two times said offset distance.

9. A surgical device for coagulating soft tissue comprising:
a first elongate member comprising a side wall with at least one lumen and at least one conductive element attached to said side wall;
at least one opening through said side wall of said first elongate member, said opening coupled to said lumen and exposing said conductive element, where the conductive element is recessed from the opening and the opening comprises a flexible portion capable of deforming to sealingly form against the soft tissue, where the opening allows soft tissue to be pulled through the opening to contact the conductive element; and wherein said conductive element comprises at least one helical winding having at least one pitch and at least one winding width.

10. The device of claim 9, where a portion of the first elongate member containing the conductive element and the conductive element are deformable.

11. The device of claim 10, where the portion of the first elongate member containing the conductive element and the conductive element are elastic.

12. The device of claim 10, where the portion of the first elongate member containing the conductive element and the conductive element are malleable.

13. The device of claim 9, wherein said side wall comprises an insulator covering.

14. The device of claim 9, wherein said conductive element comprises a series of helical windings having at least one pitch and at least one winding width;

wherein said pitch is greater than or equal to two times said width.

15. The device of claim 9, wherein said conductive element comprises a series of helical windings having at least one pitch and at least one winding width, wherein said pitch is greater than or equal to four times said width.

16. The device of claim 9 wherein the external surface of said side wall along said opening is offset from said conductive element by a distance; wherein the width of said opening is greater than or equal to said offset distance.

17. The device of claim 9 wherein the external surface of said side wall along said opening is offset from said conductive element by a distance; wherein the width of said opening is greater than two times said offset distance.

* * * * *